United States Patent
Chandrasekher et al.

(10) Patent No.: US 10,765,776 B1
(45) Date of Patent: Sep. 8, 2020

(54) TISSUE-DERIVED BIOMATERIAL COMPOSITION AND METHODS FOR OCULAR AND OTHER THERAPEUTIC APPLICATIONS

(71) Applicant: South Dakota Board of Regents (SDBOR), Pierre, SD (US)

(72) Inventors: Gudiseva Chandrasekher, Sioux Falls, SD (US); Somshuvra Bhattacharya, Brookings, SD (US)

(73) Assignee: SOUTH DAKOTA BOARD OF REGENTS (SDBOR), Pierre, SD (US)

( * ) Notice: Subject to any disclaimer, the term of this patent is extended or adjusted under 35 U.S.C. 154(b) by 255 days.

(21) Appl. No.: 15/791,720

(22) Filed: Oct. 24, 2017

(51) Int. Cl.
*A61L 27/36* (2006.01)
*A61L 27/38* (2006.01)
*A61K 35/30* (2015.01)

(52) U.S. Cl.
CPC .......... *A61L 27/3604* (2013.01); *A61K 35/30* (2013.01); *A61L 27/3687* (2013.01); *A61L 27/3691* (2013.01); *A61L 27/3808* (2013.01); *A61L 27/3813* (2013.01); *A61L 27/3886* (2013.01); *A61L 2430/16* (2013.01)

(58) Field of Classification Search
None
See application file for complete search history.

(56) References Cited

U.S. PATENT DOCUMENTS

2014/0099290 A1* 4/2014 Soker .................. A61L 27/3604
424/93.7

OTHER PUBLICATIONS

Keane, Timothy J., Ilea T. Swinehart, and Stephen F. Badylak. "Methods of tissue decellularization used for preparation of biologic scaffolds and in vivo relevance." Methods 84 (2015): 25-34. (Year: 2015).*

Howkins, Ashley, "Elucidation of Porcine Corneal Ultrastructure to Inform Development of Corneal Xenografts or Biomimetic Replacements", Thesis for University of Brighton for the degree of Doctor of Philosophy, Jun. 2015, pp. 1-245.

* cited by examiner

*Primary Examiner* — Robert J Yamasaki
(74) *Attorney, Agent, or Firm* — Mallory M. Henninger; Advent, LLP

(57) ABSTRACT

The present disclosure relates to a composition and methods for preparing a tissue-derived, dissolved extracellular matrix. In implementations, the extracellular matrix composition includes components native to the cornea including liquefied corneal tissue. The extracellular matrix composition can be prepared by dissolving extracted corneas in an aqueous solution of inorganic base. The resulting solution is then dialyzed to achieve a physiological pH. In some implementations, the extracellular matrix composition can be seeded and/or chemically cross-linked to form a gel matrix. The extracellular matrix and/or the gel matrix can be seeded with a desired cell type (e.g., endothelial cells, epithelial cells, stromal keratocytes, etc.) to stimulate cell proliferation and regeneration.

14 Claims, 11 Drawing Sheets
(5 of 11 Drawing Sheet(s) Filed in Color)

TISSUE-DERIVED BIOMATERIAL COMPOSITION AND METHODS FOR OCULAR AND OTHER THERAPEUTIC APPLICATIONS

BACKGROUND

The cornea is the clear, protective outer layer of the eye. It serves as a barrier against dirt, germs, and other particles that can harm the delicate components of the eye. The cornea is also capable of filtering out some amounts of the sun's ultraviolet light, and plays a key role in vision by refracting light that enters the eye. The cornea can be susceptible to damage or impairment through corneal disease or physical injury. Corneal diseases include a variety of conditions that affect mainly the cornea such as infections, degenerations, and many other disorders of the cornea that may arise as a result of heredity.

SUMMARY

The present disclosure relates to compositions and methods for preparing a tissue-derived, dissolved extracellular matrix. In implementations, an extracellular matrix composition includes components native to the cornea including liquefied corneal tissue. The extracellular matrix composition can be prepared by dissolving extracted corneas in an aqueous solution of inorganic base. The resulting solution is then dialyzed to achieve a physiological pH. The extracellular matrix composition can be seeded with a desired cell type (e.g., endothelial cells, epithelial cells, stromal keratocytes, etc.) to form a suspension suitable for stimulating cell proliferation.

In some implementations, the extracellular matrix composition can be blended into a gel forming chemical material (e.g., pectin-calcium gel) to form a gel matrix. The gel matrix can be seeded with a desired cell type (e.g., endothelial cells, epithelial cells, stromal keratocytes, etc.) to stimulate sustained cell proliferation and outgrowth.

In some implementations, the extracellular matrix composition can be cross-linked chemically to form a scaffold/implant (e.g., glutaraldehyde cross-linked extracellular matrix composition). The scaffold/implant can be seeded with a desired cell type (e.g., endothelial cells, epithelial cells, stromal keratocytes, etc.) to stimulate sustained cell proliferation.

In some implementations, the extracellular matrix can be utilized in the treatment of ocular disorders to stimulate cell regeneration. In other implementations, the extracellular matrix can be utilized in the treatment of non-ocular disorders which require an environment rich in healthy extracellular matrix.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The patent or application file contains at least one drawing executed in color. Copies of this patent or patent application publication with color drawing(s) will be provided by the Office upon request and payment of the necessary fee.

The detailed description is described with reference to the accompanying figures. The use of the same reference numbers in different instances in the description and the figures may indicate similar or identical items.

DETAILED DESCRIPTION

Definitions

Figure 1:
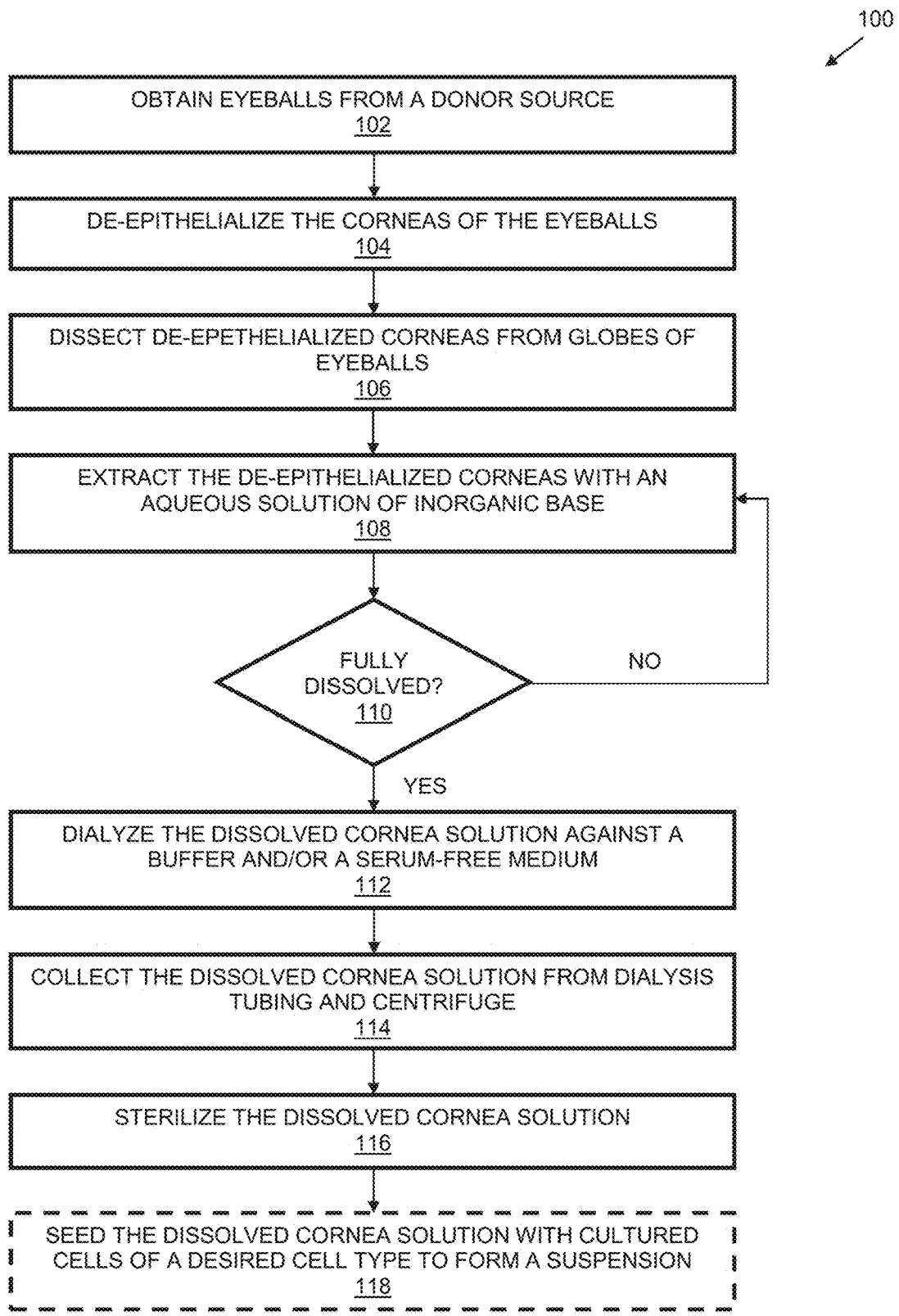
FIG. 1 is a flow diagram illustrating an example method for preparing an extracellular matrix composition in accordance with exemplary embodiments of the present disclosure.

For the following defined terms, these definitions shall be applied, unless a different definition is provided elsewhere in the specification or in the claims.

All numeric values used herein are assumed to be modified by the term "about," whether or not explicitly indicated. The term "about" generally refers to a range of numbers that one of skill in the art would consider equivalent to the recited value (i.e., having the same function or result) of the individual ingredient, the composition, or the embodiment. Thus, the term "about" can refer to a variation of ±5%, ±10%, ±20%, or ±25% of the value specified. For integer ranges, the term "about" can include one or two integers greater than and/or less than the integer recited at each end of a specified range. In many instances, the term "about" may include numbers that are rounded to the nearest significant figure.

As used herein and in the appended claims, the singular forms "a," "an," and "the" include plural referents unless the context clearly dictates otherwise.

As used herein and in the appended claims, the term "or" is generally employed in its sense including "and/or" unless the context clearly dictates otherwise.

The terms "treating," "treat," and "treatment," as used herein, include (i) preventing a disease, pathologic or medical condition from occurring (e.g., prophylaxis); (ii) inhibiting the disease, pathologic or medical condition, or slowing the progression of or arresting its development; (iii) relieving the disease, pathologic or medical condition; and/or (iv) decreasing symptoms associated with the disease, pathologic or medical condition. Thus, the terms "treat," "treatment," and "treating" can extend to prophylaxis and can include prevent, prevention, preventing, reducing, stopping or reversing the progression or severity of the condition and/or symptoms being treated. As such, the term "treatment" can include medical, therapeutic, and/or prophylactic administration, as appropriate.

Overview

The term "corneal disease" refers to a variety of conditions that affect mainly the cornea. These include infections, degenerations, and many other disorders of the cornea that may arise as a result of heredity. The cornea can also be damaged due to injury.

The term "corneal dystrophy" includes a rare group of hereditary non-inflammatory corneal diseases restricted to the cornea. Corneal dystrophies can be clinically grouped into three categories based on the predominant anatomical location of abnormalities: those affecting primarily the corneal epithelial cells, the basement membrane or Bowman layer of the corneal epithelium, or the superficial corneal stroma (anterior corneal dystrophies); those affecting primarily corneal stromal cells (stromal corneal dystrophies); and those affecting primarily corneal endothelial cells or the Descemet membrane (posterior corneal dystrophies). These disorders are often progressive and result in the abnormal accumulation of material in the otherwise transparent cornea.

Keratoconus is a common type of cornea dystrophy. Keratoconus results from an altered configuration of collagen fibers present in the corneal stroma extracellular matrix, causing the middle portion of the cornea to thin and gradually bulge outward, forming a rounded cone shape. Cone formation contributes to symptoms such as distorted vision, increased sensitivity to glare and light, and reduction in visual acuity.

Recurrent corneal erosion syndrome (RCES) is a common disorder involving the corneal epithelium and the epithelial basement membrane. Recurrent corneal erosion can result from trauma, epithelial basement membrane dystrophy (EBMD), or a combination thereof. Patients with EBMD have an anterior epithelium that does not adhere well to the basement membrane, as a result of abnormalities in the extracellular matrix composition or synthesis in the epithelial cells or the basement membrane, or damage to the basement membrane.

Treatment options for severe cases of corneal dystrophy, RCES, and other corneal disorders are limited, particularly for those disorders that arise due to impairment in the regeneration and/or attachment of cells on the surface or inside of the cornea. The success of most treatments for epithelial dystrophies is dependent on the ability of the epithelial cells to regenerate. Additionally, human endothelial cells typically do not have the capacity to regenerate. Corneal transplant or partial corneal transplant is the most common curative treatment available for severe cornea disorders. While corneal transplants can be successful, surgery presents significant risk to the patient, and the foreign tissue can incite an immunogenic response. There are no pharmaceutical compositions available that exactly mimic native corneal tissue components, and compositions that utilize exogenous chemicals can produce toxic and/or immunogenic responses.

The present disclosure relates to a composition and methods for preparing a tissue-derived, dissolved extracellular matrix. In implementations, the extracellular matrix composition includes components native to the cornea including liquefied corneal tissue. The extracellular matrix composition can be prepared by dissolving extracted corneas in an aqueous solution of inorganic base. The resulting solution is then dialyzed to achieve a physiological pH. In some implementations, the extracellular matrix composition can be seeded and/or chemically cross-linked to form a gel matrix. The extracellular matrix and/or the gel matrix can be seeded with a desired cell type (e.g., endothelial cells, epithelial cells, stromal keratocytes, etc.) to stimulate cell proliferation and regeneration.

EXAMPLE IMPLEMENTATIONS

The extracellular matrix composition and methods may be further clarified by reference to the following Examples, which serve to exemplify some of the preferred embodiments, and not to limit the disclosure in any way.

Example 1

General Method of Preparing an Extracellular Matrix Composition.

FIG. 1 illustrates by means of a flow chart an example method 100 for preparing an extracellular matrix composition in accordance with the present disclosure. One or more eyeballs are obtained from a donor source (Block 102). In example implementations, eyeballs can be obtained from pigs. However, the use of pig eyeballs as the tissue source is offered by way of example only and is not meant to be restrictive of the present disclosure. In other implementations, the eyeballs can be obtained from other animal sources or human donors.

The corneas are de-epithelialized (Block 104). De-epithelializing the corneas includes removing most or all of the epithelium. A negligible amount of epithelium may be present without impacting the efficacy of the composition. De-epithelializing the corneas provides an exposed stromal layer rich in extracellular matrix. The de-epithelialized corneas are dissected from the globes of the eyeballs (Block 106).

The de-epithelialized corneas are extracted with an aqueous solution of inorganic base (e.g., sodium hydroxide solution; Block 108). In a specific implementation, the de-epithelialized corneas can be extracted with about 2.37 mL of 1N sodium hydroxide (NaOH) per cornea. It is contemplated that the de-epithelialized corneas may be extracted with other amounts and/or concentrations of NaOH and/or with other materials. The de-epithelialized corneas are assessed periodically or continually to determine if they are fully dissolved (Decision Block 110). If the de-epithelialized corneas are not fully dissolved (No to Decision Block 110), extraction with the aqueous solution of inorganic base is continued until fully dissolved. In some specific implementations, the corneas can be fully dissolved within about 14 to about 16 days.

If the de-epithelialized corneas are fully dissolved (Yes to Decision Block 110), then the dissolved cornea solution is dialyzed against a buffer until the dissolved cornea solution is adjusted to a physiologic pH (e.g., about 7.4; Block 112). Suitable buffers include, but are not necessarily limited to: (e.g., 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), etc.) and/or a serum-free medium (e.g., Dulbecco's Modified Eagle's Medium (DMEM), Eagle's Minimum Essential Medium (EMEM), Roswell Park Memorial Institute 1640 Medium (RPMI-1640), Ham's F10 Nutrient Mixture (Ham's F10), Ham's F12 Nutrient Mixture (Ham's F12), a 1:1 mixture of DMEM and Ham's F12 (DMEM/F12), and so forth. In one specific implementation, the dissolved cornea solution can be dialyzed against 15 mM HEPES buffer for about 24 hours, followed by dialysis against serum-free DMEM/F12 for about 24 hours. It is contemplated that other buffers and/or materials and other times can be utilized to dialyze the dissolved cornea solution.

The dissolved cornea solution is collected from the dialysis tubing and centrifuged (Block 114). In a specific exemplary implementation, the dissolved cornea solution can be collected into 1.5 ml tubes and centrifuged for about 20 min at about 14,000 rpm. In other implementations, the dissolved cornea solution can be centrifuged with other speeds and/or durations. The dissolved cornea solution is sterilized to remove contaminants (Block 116). In specific exemplary implementations, the dissolved cornea solution was sterilized by UV light sterilization for about 6 to about 8 hours. However, the use of UV sterilization is offered by way of example only and is not meant to be restrictive of the present disclosure. In other implementations, other suitable sterilization techniques can be utilized including, but not necessarily limited to: moist heat sterilization, microfiltration, and so forth. Further, the length of sterilization time can vary depending on the sterilization technique selected, requisite purity level of the end product, and so forth. The resultant extracellular matrix composition is a transparent solution including native cornea components that can be useful in treating ocular disorders. The transparent nature of the solution is significant in terms of mimicking the transparent nature of the cornea. In specific instances, the extracellular matrix composition can be stored at a temperature of about −20 degrees Celsius.

In some implementations, the sterilized dissolved cornea solution may be seeded (e.g., mixed) with cultured tissue cells of a desired cell type (e.g., epithelial cells, endothelial cells, stromal keratocytes, etc.) to form a suspension (Block 118). For example, the dissolved cornea solution can be seeded with cultured corneal cells (e.g., corneal epithelial cells, corneal endothelial cells, corneal stromal keratocytes, etc.). Because the sterilized dissolved cornea solution is rich in extracellular matrix components native to the cornea, it can stimulate proliferation of the seeded cells.

Example 2

Components of the Extracellular Matrix Composition Derived from Corneal Tissue.

Because the extracellular matrix composition includes primarily dissolved corneal tissue, the extracellular matrix composition approximates the composition of mature (e.g., adult) cornea tissue. In some implementations, the extracellular matrix composition can include collagens in the range of about 85% to about 95% of the total protein mass of the solution. In one specific implementation, the amount of collagens in the extracellular matrix composition can be about 90% of the total protein mass of the solution. The collagens may primarily consist of collagen types I, III, V, and VI, with a ratio of collagen type to total corneal collagens of about 75% to about 85% collagen type I, about 1% to about 10% collagen type V, and about 10% to about 20% collagen type VI, although other ratios may be employed. In one specific implementation, the ratio of collagen type to total corneal collagens is about 75% to about 85% collagen type I, about 1% to about 2% collagen type V, and about 15% collagen type VI. Other collagen types identified in corneal tissue in smaller amounts may include collagen types IV, IX, XII, and XIV. The extracellular matrix composition can also include extracellular matrix proteins present in corneal tissue including, but not necessarily limited to, laminin, fibronectin, and so forth. The extracellular matrix composition can also include non-extracellular matrix proteins present in the cornea (e.g., corneal crystallin). In embodiments, the extracellular matrix composition can include proteins other than collagens in a range of about 5% to about 15% of the total protein mass of the solution.

The extracellular matrix composition can also include proteoglycans (e.g., mucopolysaccharides) found in corneal tissue. The proteoglycans can include protein components such as decorin, biglycan, lumican, keratocan, fibromodulin, and so forth. Decorin and biglycan can include carbohydrate components such as dermatan sulphate and chondroitin sulphate. Lumican, keratocan, and fibromodulin can include carbohydrate components such as keratan sulphate. The ratio of chondroitin sulphate to keratan sulphate can be about 30% to about 40% chondroitin sulphate to about 60% to about 70% keratan sulphate, although other ratios may be employed. In some specific implementations, the ratio of chondroitin sulphate to keratan sulphate can be about 37% chondroitin sulphate to about 63% keratan sulphate.

Figure 2A:
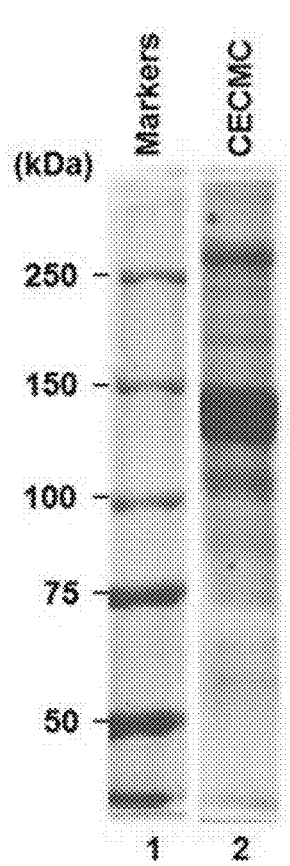
FIG. 2A is a Sodium dodecyl sulfate polyacrylamide gel electrophoresis (SDS-PAGE) assay depicting native corneal protein components present in an extracellular matrix composition in accordance with exemplary embodiments of the present disclosure.
Figure 2B:
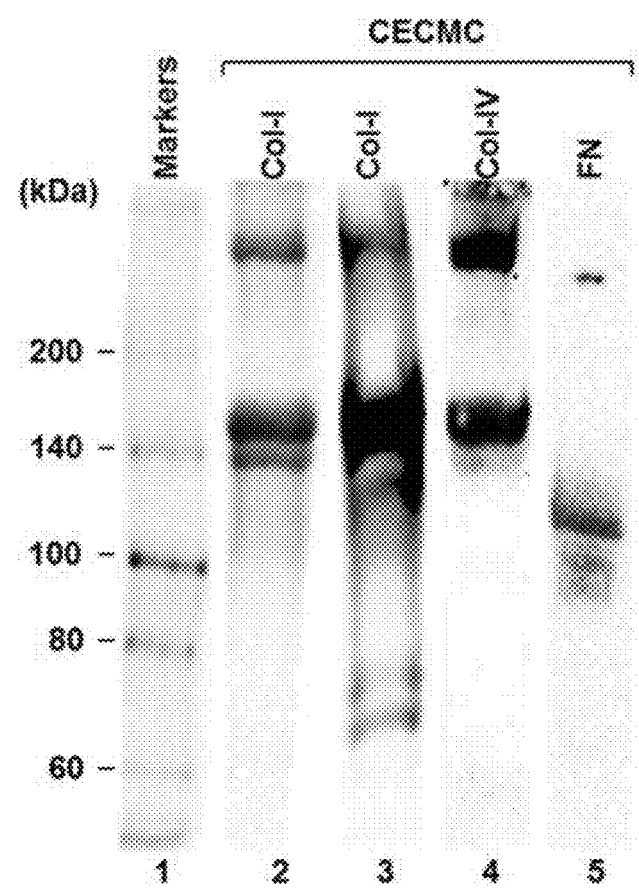
FIG. 2B is a western immunoblot assay depicting native corneal protein components collagen I, collagen IV and fibronectin present in an extracellular matrix composition in accordance with exemplary embodiments of the present disclosure.

FIG. 2 A illustrates an exemplary polyacrylamide gel electrophoresis (PAGE) assay of the extracellular matrix composition. Lane 1 indicates molecular weight markers. Lane 2, indicates the presence of corneal proteins of different molecular weight that are stained with coomassie brilliant blue dye. FIG. 2B illustrates an exemplary Western immunoblots of the extracellular matrix composition probed with anti-collagen I antibody, anti-collagen IV antibody and anti-fibronectin antibody. Lane 1 indicates molecular weight markers. Lane 2 shows the presence of collagen I polypeptide of >250 kDa and ~140 kDa, lane 3 shows the presence of the collagen I polypeptides of >250 kDa, ~140 kDa and 65-75 kDa, lane 4 indicates collagen IV (>250 kDa and ~140 kDa), and lane 5 indicates fibronectin (~120 kDa), respectively. Because the extracellular matrix composition includes components native to corneal tissue, it can be useful in the treatment of ocular disorders. A composition derived from native corneal tissue components can reduce the occurrence of immunogenic responses resulting from the presence of foreign materials (e.g., exogenous chemicals).

It is to be understood that the components present in the extracellular matrix composition are offered by way of example only and are not meant to be restrictive of the present disclosure. In other embodiments, the types and amounts of collagens, proteins, and carbohydrates present in the extracellular matrix can vary depending on the tissue source (e.g., human, animal, etc.), and/or the maturity of tissue (e.g., adult, juvenile, etc.).

Example 3

Ex Vivo Proliferative Effects of the Extracellular Matrix Composition in Corneal Epithelial Cells.

In this example, the extracellular matrix composition was seeded (e.g., mixed) with corneal epithelial cells to form a suspension. The suspension was layered onto the surface of corneas de-epithelialized by debridement (e.g., removal of the epithelial layer surface). De-epithelializing the corneas includes removing most or all of the epithelium. A negligible amount of epithelium may be present without impacting the efficacy of the composition. After a growth period of approximately 24 to 72 hours, the corneal surface was examined by microscope.

Figure 3A:
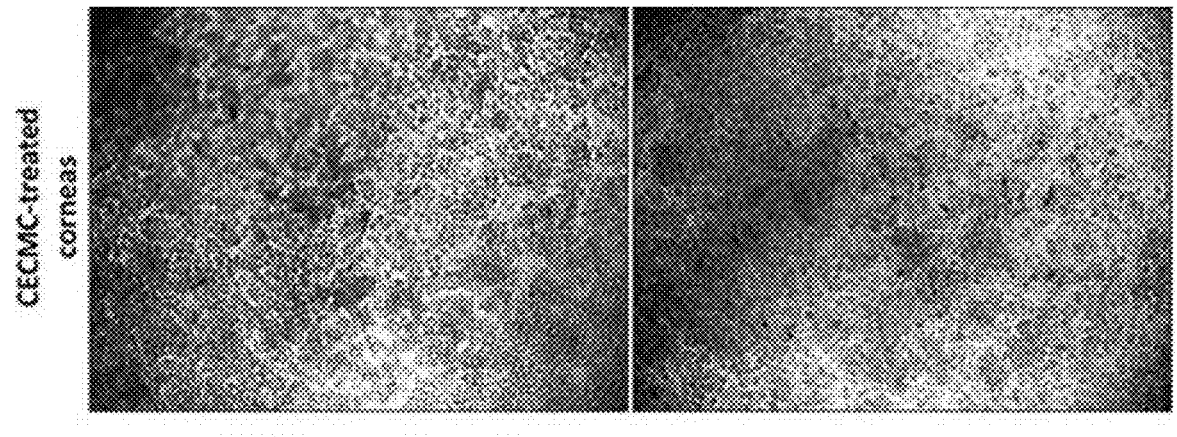
FIG. 3A is a microscopy depiction of growth on the surface of de-epithelialized pig cornea of pig corneal epithelial cells seeded with an extracellular matrix composition in accordance with exemplary embodiments of the present disclosure.
Figure 3B:
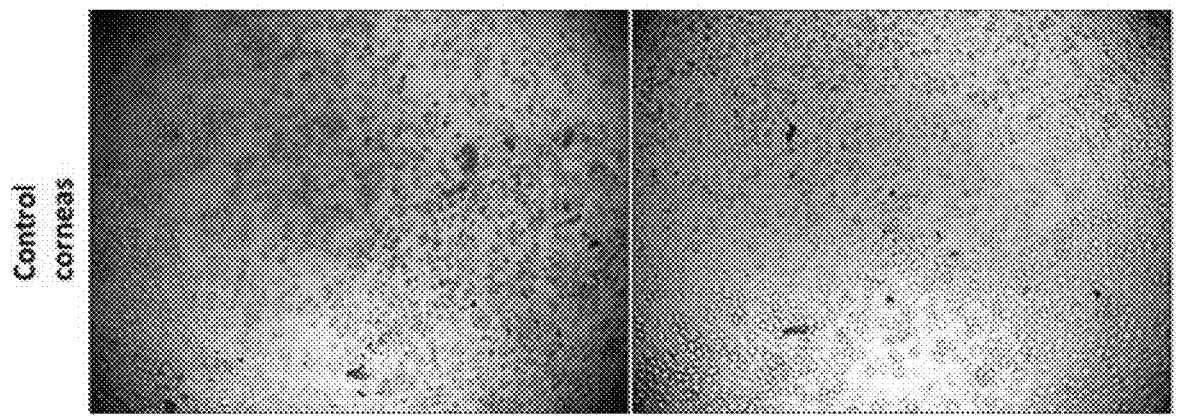
FIG. 3B is a microscopy depiction of growth on the surface of de-epithelialized pig corneas of pig corneal epithelial cells seeded without an extracellular matrix composition in accordance with exemplary embodiments of the present disclosure.

FIGS. 3A and 3B illustrate microscopy depictions of the surface of pig corneas treated with the extracellular matrix composition suspension including pig corneal epithelial cells and control pig corneas treated with pig corneal epithelial cell suspension devoid of extracellular matrix composition, respectively. As illustrated in FIG. 3A, in corneas treated with the extracellular matrix composition suspension attachment and growth of corneal epithelial cells (e.g., granule-like structures) over the underlying stromal layer containing keratocytes was robust compared to control corneas (FIG. 3B). Further, the epithelial cells on treated corneas grew and organized in the form of a sheet that mimics the organization of the natural corneal epithelial cell layer. The attachment and growth of epithelial cells on untreated control corneas is weak and numerous de-epithelialized regions were easily visible when viewed under the microscope.

Figure 4A:
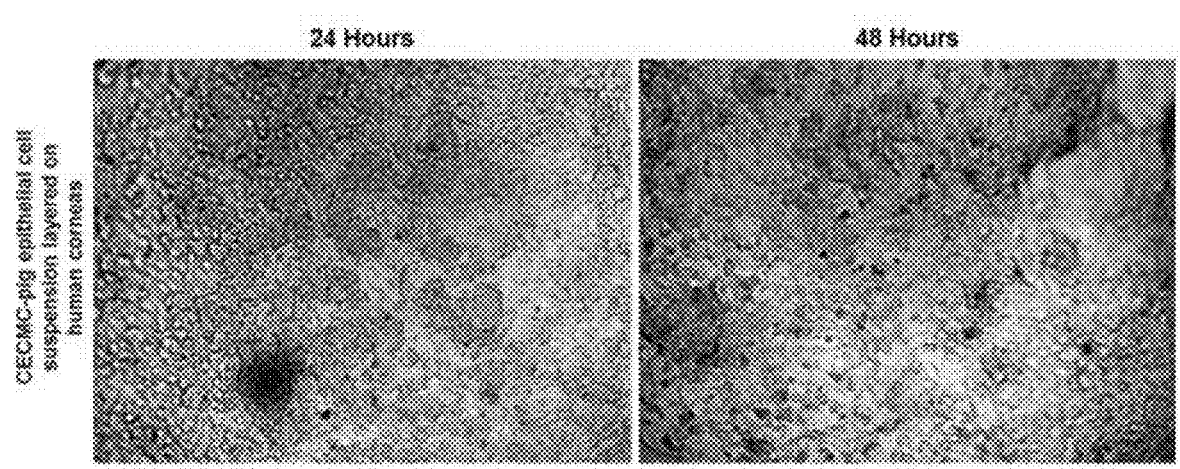
FIG. 4A is a microscopy depiction of growth on the surface of de-epithelialized human cornea of corneal epithelial cells seeded with an extracellular matrix composition including pig epithelial cells in accordance with exemplary embodiments of the present disclosure.
Figure 4B:
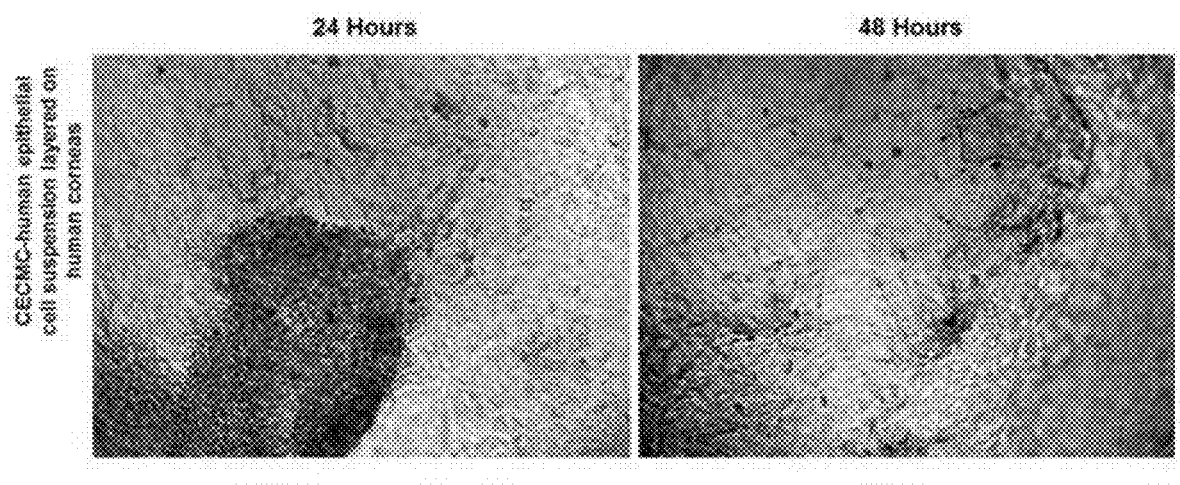
FIG. 4B is a microscopy depiction of growth on the surface of de-epithelialized human cornea of corneal epithelial cells seeded with an extracellular matrix composition including human epithelial cells in accordance with exemplary embodiments of the present disclosure.

FIGS. 4A and 4B illustrate microscopy depictions of the surface of human corneas treated with extracellular matrix composition suspension including pig epithelial cells and extracellular matrix composition suspension including human epithelial cells, respectively. As illustrated in FIG. 4A, in corneas treated with the extracellular matrix composition suspension including pig epithelial cells, attachment and growth of corneal epithelial cells (e.g., granule-like structures) over the underlying stromal layer containing keratocytes was robust at both 24 hours and 48 hours post-treatment. As illustrated in FIG. 4B, in corneas treated with the extracellular matrix composition suspension including human epithelial cells, attachment and growth of corneal epithelial cells (e.g., granule-like structures) over the underlying stromal layer was also robust at both 24 hours and 48 hours post-treatment.

Figure 5A:
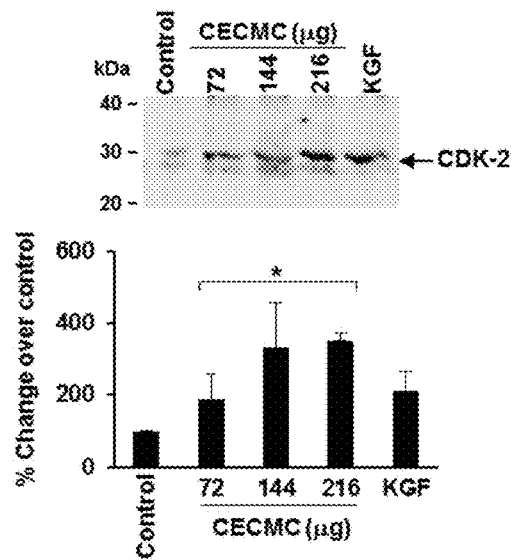
FIG. 5A is a Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5B:
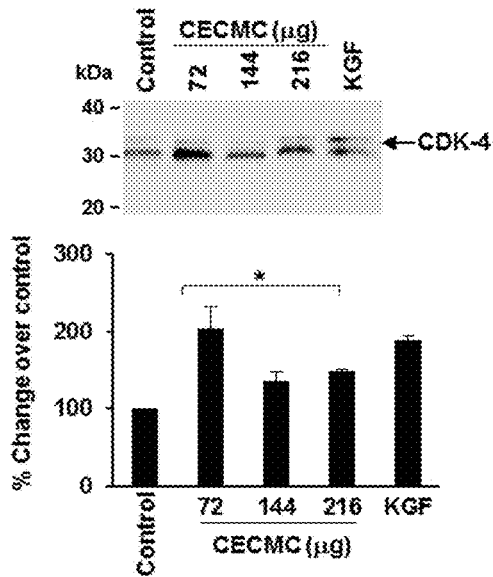
FIG. 5B is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5C:
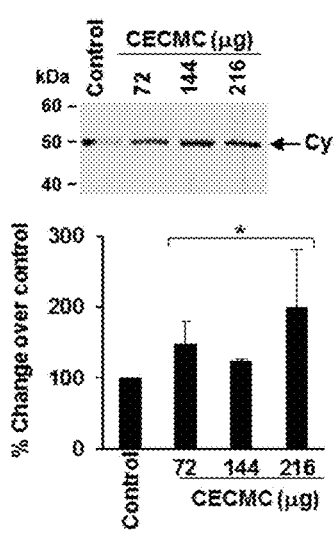
FIG. 5C is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5D:
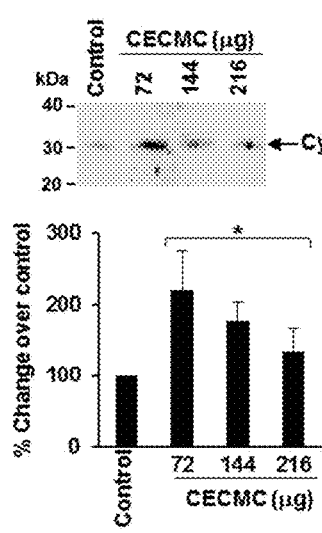
FIG. 5D is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5E:
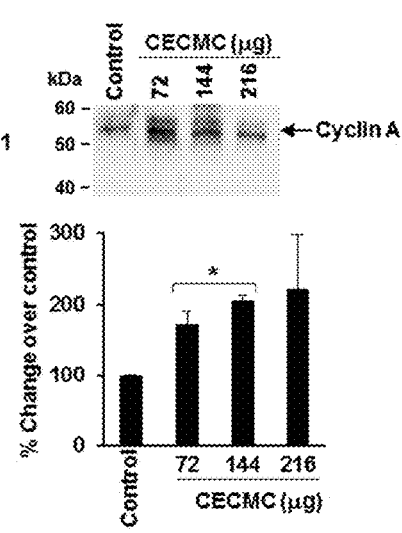
FIG. 5E is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5F:
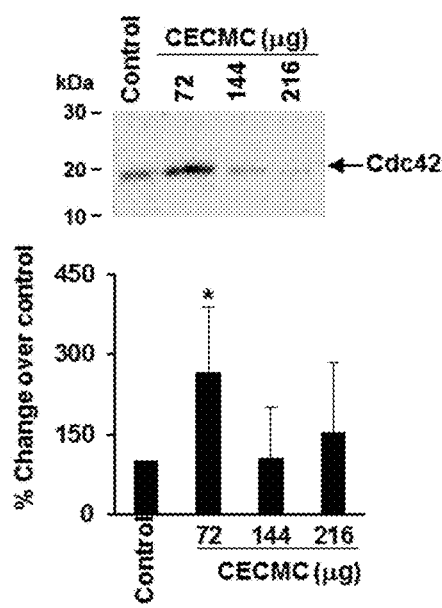
FIG. 5F is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.
Figure 5G:
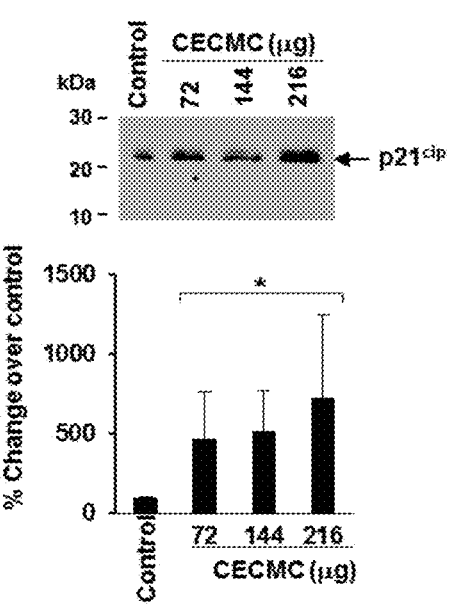
FIG. 5G is another Western blot assay and corresponding bar graph depicting the expression of cell cycle proteins in cultured untreated control corneal epithelial cells and corneal epithelial cells treated with an extracellular matrix composition in accordance with exemplary embodiments of the present disclosure.

FIGS. 5A through 5G illustrate Western blot analysis and corresponding bar graphs representing the percent changes in the expression levels of cell cycle proteins (e.g., CDK-2, CDK-4, cyclin E, cyclin D1, cyclin A, Cdc42, p21$^{cip}$, etc.) in untreated control primary corneal epithelial cell cultures and primary corneal epithelial cell cultures treated with different concentrations of the extracellular matrix composition suspension (e.g., 72 µg/mL, 144 µg/mL, 216 µg/mL). Epithelial cell cultures treated with keratinocyte growth factor (KGF, 10 ng/mL), an accelerator of epithelial cell proliferation, were used to show cell cycle proteins that would be elevated with epithelial cell proliferation. The untreated corneal epithelial cell cultures were used as a control group. FIGS. 5A through 5D and FIG. 5G show a statistically significant increase in expression of CDK-2, CDK-4, cyclin E, cyclin D1, and p-21$^{cip}$, respectively, at all concentrations. FIGS. 5A and 5B also depict statistically significant increase in expression of CDK-2 and CDK-4, in KGF treated epithelial cultures (p<0.05). FIG. 5E shows a statistically significant increase in expression of cyclin A in the 72 µg/mL and 144 µg/mL treated epithelial cultures. FIG. 5F shows a statistically significant increase in expression of Cdc42 in the 72 µg/mL treated epithelial cultures (p<0.05). During new cell generation, cell cycle protein synthesis increases to facilitate cell division. Thus, post-treatment elevated cell cycle proteins expression is suggestive of proliferation promotion capability of extracellular matrix composition.

Figure 6A:
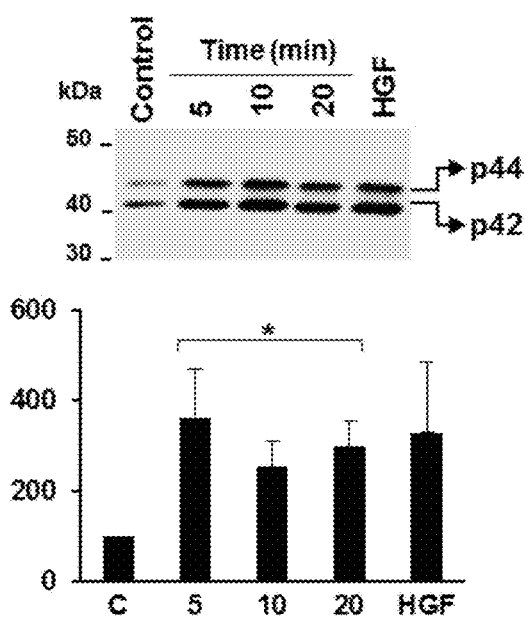
FIG. 6A is a Western blot assay and corresponding bar graph depicting the activation of intracellular signal mediators in cultured untreated control corneal epithelial cells and corneal epithelial cells treated with an extracellular matrix composition in accordance with exemplary embodiments of the present disclosure.
Figure 6B:
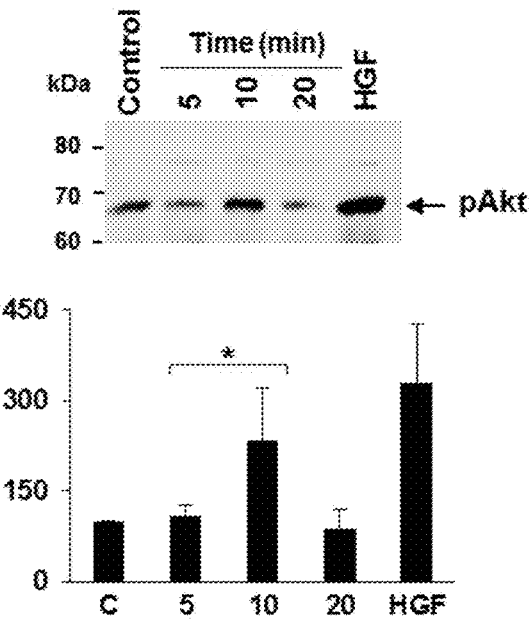
FIG. 6B is another Western blot assay and corresponding bar graph depicting the activation of intracellular signal mediators in cultured untreated control corneal epithelial cells and corneal epithelial cells treated with an extracellular matrix composition in accordance with exemplary embodiments of the present disclosure.

FIGS. 6A and 6B illustrate an exemplary Western blot analysis and corresponding bar graph representations of critical intracellular signal mediator (e.g., Erk1, Erk2, Akt, etc.) activation over different treatment time periods (e.g., 5-20 minutes) in primary corneal epithelial cell cultures treated with the extracellular matrix composition (e.g., 144 µg/mL). Corneal epithelial cells treated with hepatocyte growth factor (HGF, 10 ng/mL), a stimulator of intracellular signal mediator activation, were used to show intracellular signal mediators that would be activated in epithelial cell proliferation. The untreated corneal epithelial cells were used as a control group. FIG. 6A indicates a statistically significant increase in p44 and p42 (i.e., activated ERK1 and ERK2, respectively) at all treatment time periods, and in HGF treated cells. FIG. 6B indicates a statistically significant increase in pAkt (i.e., activated Akt) at all treatment time periods. Activation of intracellular signal mediators is prerequisite for the increased expression of cell cycle proteins. Thus, increased activation of intracellular signal mediators and increased synthesis of cell cycle proteins after treatment with extracellular matrix composition could be the reason for increased proliferation and growth of corneal epithelial cells on de-epithelialized corneas shown in FIG. 3A.

Example 4

General Method for Preparing a Pectin Gel Scaffold to Support the Sustained Growth of Corneal Epithelial Cells.

Figure 7:
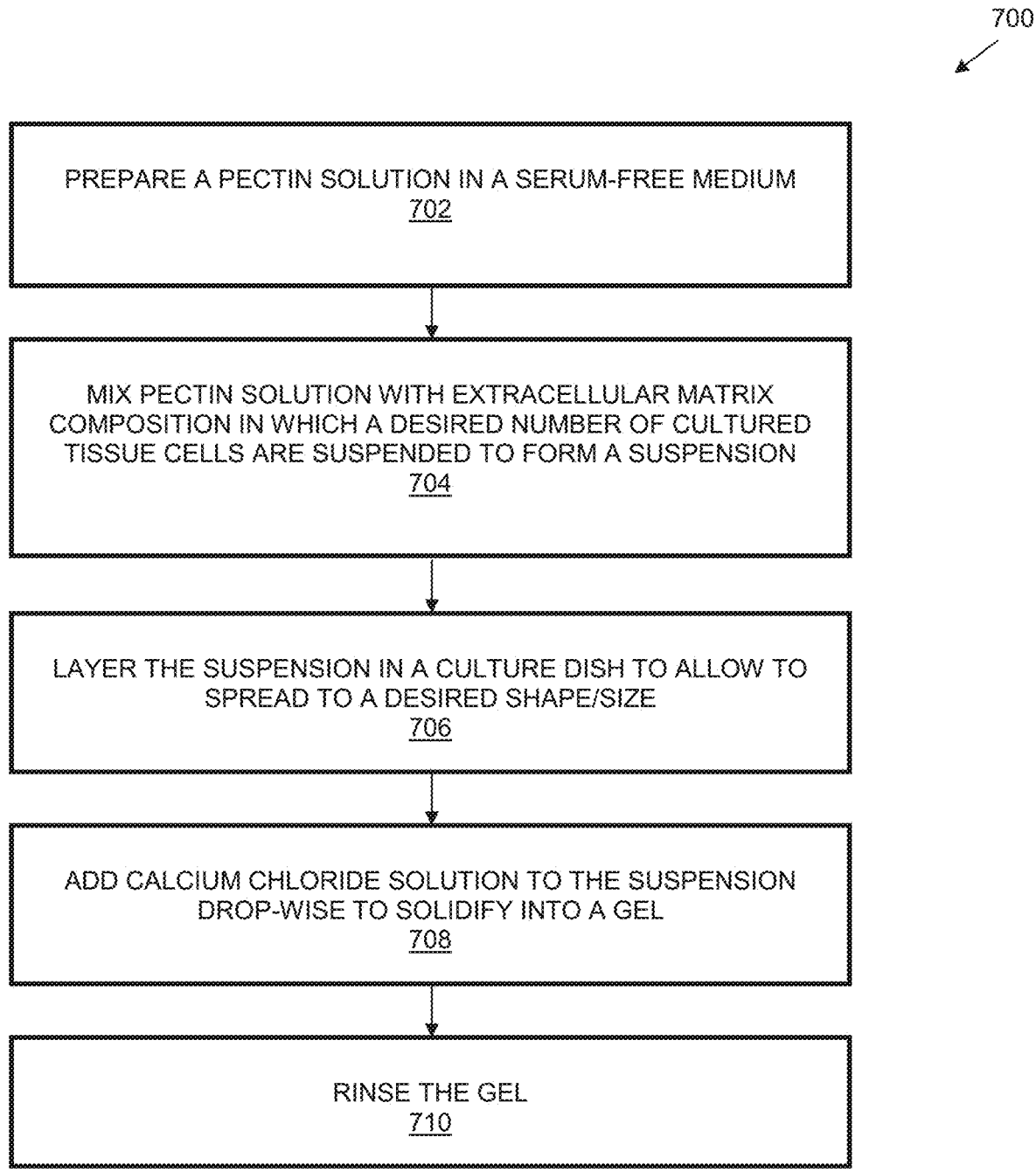
FIG. 7 is a flow diagram illustrating an example method for preparing the seeding of corneal epithelial cells in an extracellular matrix composition blended in a pectin-calcium gel matrix in accordance with exemplary embodiments of the present disclosure.

FIG. 7 illustrates by means of a flow chart an example method 700 for preparing a gel matrix scaffold that can support the sustained growth of corneal epithelial cells in accordance with the present disclosure. In implementations, a pectin solution is prepared in a serum-free medium (e.g., DMEM, EMEM, RPMI-1640, Ham's F-10, Ham's F-12, DMEM/F12, etc.; Block 702). In specific implementations, a 1.75% pectin solution (wt/vol) can be used. However, this concentration is offered by way of example only and is not meant to restrict the present disclosure. In other implementations, other concentrations of pectin solution can be utilized. A suspension is formed by mixing the pectin solution with an extracellular matrix composition in which a desired number of cultured tissue cells (e.g., epithelial cells, endothelial cells, stromal cells, etc) are suspended (Block 704). In example implementations, the gel matrix can be seeded with corneal cells (e.g., corneal epithelial cells, corneal endothelial cells, corneal stromal keratocytes, etc.). In specific implementations, the pectin solution can be mixed with a 2.7 mg/ml extracellular matrix composition (1:1 volume ratio). In some implementations, the desired cell density of suspended cells can be approximately $10^6$ cells per ml. The suspension is layered (e.g., drop-wise) in a culture dish to allow to spread to a desired shape/size (Block 706). For example, the suspension can be allowed to spread to a circular shape approximately ¼ inch in diameter. A calcium chloride solution is then added drop-wise to the suspension to solidify the suspension into a gel (Block 708). In some implementations, the calcium chloride solution can be prepared in a serum-free medium. In one specific implementation, a 1% calcium chloride solution (wt/vol) can be used. However, this concentration is offered by way of example only and is not meant to restrict the present disclosure. In other implementations, other concentrations of calcium chloride solution can be utilized. Excess calcium chloride can be drained from the gel matrix. The gel is then rinsed (Block 710). Rinsing removes non-adhering cells from the surface of the gel. In some implementations, the gel can be rinsed with serum-free medium.

Figure 8A:
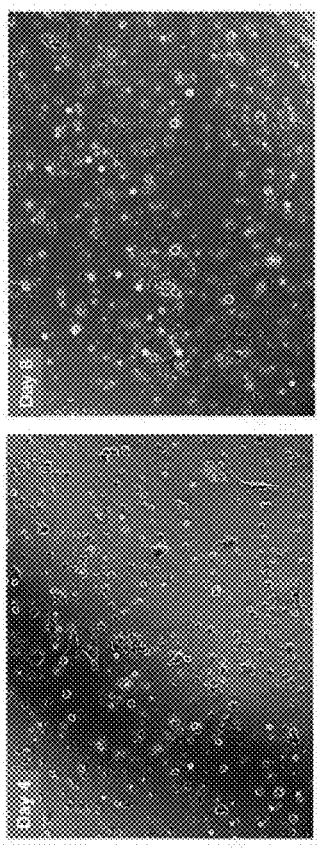
FIG. 8A is a microscopy depiction of seeded corneal epithelial cell growth in pectin gel matrix prepared without an extracellular matrix composition in accordance with exemplary embodiments of the present disclosure.
Figure 8B:
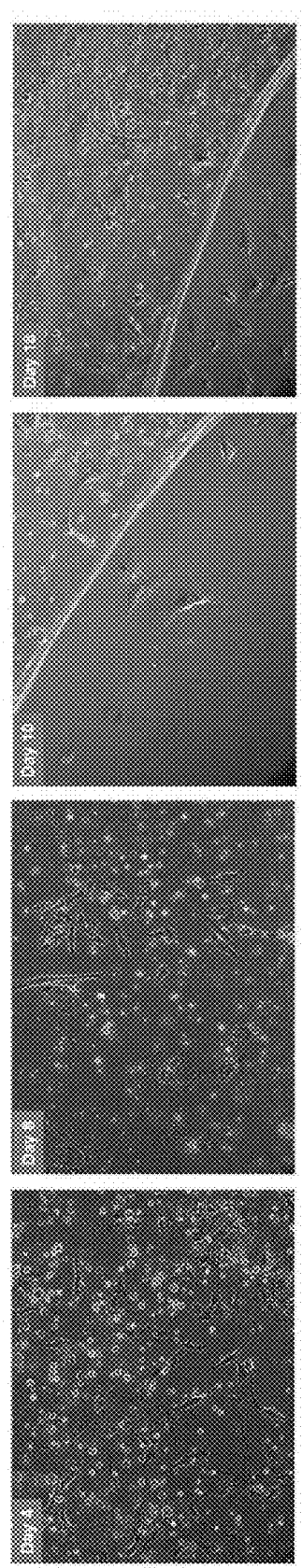
FIG. 8B is a microscopy depiction of seeded corneal epithelial cell growth in pectin gel matrix prepared with an extracellular matrix composition in accordance with exemplary embodiments of the present disclosure.

FIGS. 8A and 8B are microscopic depictions illustrating a specific example of corneal epithelial cell proliferation in a pectin-calcium gel matrix seeded with the extracellular matrix composition and corneal epithelial cells compared to control pectin-calcium gel matrix seeded with corneal epithelial cells without extracellular matrix composition. The control untreated gels showed only minimal corneal epithelial cell proliferation, as illustrated in FIG. 8A. The seeded gel matrix stimulated both in-gel proliferation of corneal epithelial cells and outgrowth from the seeded gel matrix, as illustrated in FIG. 8B. Epithelial cell proliferation was visible as early as day 2, and epithelial outgrowth from the seeded gel matrix was sustained for a period of 7 to 10 days. Growth of corneal epithelial cells in the control untreated gels was very minimal beyond 8 days. Sustained cell-regenerating potential of the extracellular matrix composition can be useful for treating difficult-to-heal corneal epithelial injuries requiring sustained cell proliferation.

Example 5

General Method for Preparing a Cross-Linked Scaffold to Support the Sustained Growth of Corneal Epithelial Cells.

Figure 9:
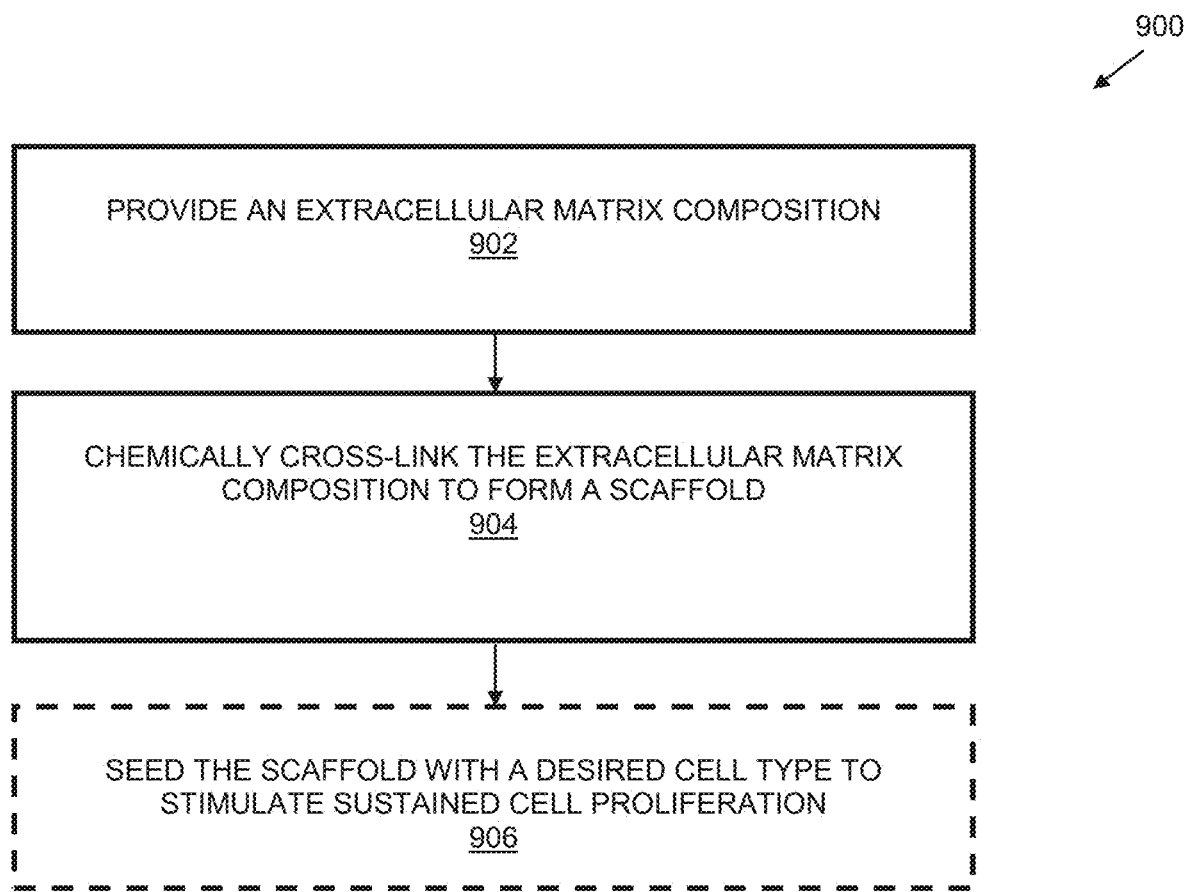
FIG. 9 is a flow diagram illustrating an example method for preparing a chemically cross-linked gel matrix scaffold from an extracellular matrix composition in accordance with exemplary embodiments of the present disclosure.

FIG. 9 illustrates by means of a flow chart an example method 900 for preparing a cross-linked matrix scaffold that can support the sustained growth of tissue cells in accordance with the present disclosure. An extracellular matrix composition is provided (Block 902). As described above, the extracellular matrix composition includes primarily dissolved corneal tissue and approximates the composition of mature (e.g., adult) cornea tissue. In example implementations, the extracellular matrix composition can be prepared utilizing the method illustrated in FIG. 1.

The extracellular matrix composition is chemically cross-linked to form a scaffold (Block 904). In embodiments, the extracellular matrix composition can be chemically cross-linked utilizing a cross-linking compound (e.g., glutaraldehyde, formaldehyde, epoxy compounds, dialdehyde, etc.) to form a gel matrix (e.g., hydrogel). The extracellular matrix composition can be cross-linked to a desired consistency (e.g., soft to hard) depending on the desired treatment application. In implementations, the scaffold can be used to support the sustained regeneration of tissue cells and/or as an implant.

In some implementations, the scaffold can be seeded with a desired cell type (e.g., endothelial cells, epithelial cells, stromal keratocytes, etc.) to stimulate sustained cell proliferation (Block 906). For example, the dissolved cornea solution can be seeded with cultured corneal cells (e.g., corneal epithelial cells, corneal endothelial cells, corneal stromal keratocytes, etc.).

Figure 10A:
FIG. 10A is a microscopy depiction of a scaffold including cross-linked extracellular matrix composition in accordance with exemplary embodiments of the present disclosure.
Figure 10B:
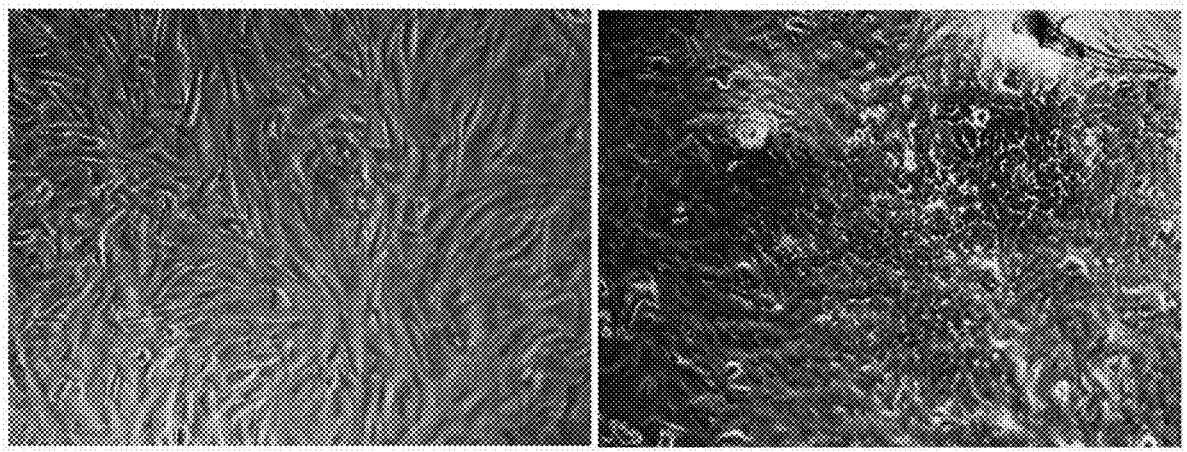
FIG. 10B is a microscopy depiction of growth of corneal epithelial cells on a cross-linked scaffold, such as the scaffold illustrated in FIG. 9, seeded with epithelial cells in accordance with exemplary embodiments of the present disclosure.

FIGS. 10A and 10B are microscopic depictions illustrating a specific example of corneal epithelial cell proliferation on glutaraldehyde cross-linked hydrogel matrix scaffold. FIG. 10A illustrates a glutaraldehyde cross-linked hydrogel matrix prior to seeding. As illustrated in FIG. 10B, attachment and growth of corneal epithelial cells (e.g., granule-like structures) on cross-linked scaffolds seeded with epithelial cells, was robust at both day 2 and day 5 post-treatment. Further, by day 5 the epithelial cells grew and organized in the form of a sheet that mimics the organization of the natural corneal epithelial cell layer.

Example 6

Extracellular Matrix Composition as Preventative and/or Therapeutic Treatment for Ocular and Other Tissue Disorders.

In some embodiments, the extracellular matrix composition can be used as a therapeutic treatment for a variety of ocular disorders. For example, the extracellular matrix can be used to stimulate cell proliferation following cell loss or damage due to injury, dystrophy, erosion, and so forth. In embodiments, the extracellular matrix composition and/or the gel matrix can be seeded with a cell type (e.g., epithelial, endothelial, stromal, etc.) selected based upon the disorder to be treated. In some embodiments, the extracellular matrix composition and/or gel matrix can be embedded with epithelial cells, as described herein, to treat corneal disorders resulting from damage to epithelial cells (e.g., anterior corneal dystrophies, RCES, etc.). However, while the figures and examples disclosed herein are directed towards stimulating corneal epithelial cell proliferation, the extracellular matrix composition and/or gel matrix can be seeded with other cell types (e.g., endothelial, stromal etc.) to treat disorders of the stroma (e.g., stromal corneal dystrophies, damage resulting from injury, etc.) or endothelial cell disorders (e.g., posterior corneal dystrophies, damage resulting from injury, etc.).

In some embodiments, the extracellular matrix composition can be used to form cornea cross-linked scaffold for sustained regeneration of cells. For example, the extracellular matrix composition can be chemically cross-linked to a desired consistency (e.g., soft to hard) to form a gel matrix, such as the gel matrix illustrated in FIGS. 10A through 10B. In implementations, the cross-linked gel matrix can be implanted inside the cornea as an ocular implant. Implantable devices formed from the extracellular matrix composition can be long-lasting and can provide the hardness necessary to prevent excessive elasticity. In some embodiments, cross-linked implantable device material can be seeded with corneal stromal keratocytes capable of secreting normal collagens. Implantable devices formed from the extracellular matrix composition and/or the gel matrix composition, and implantable devices seeded with stromal keratocytes can be useful in the treatment of corneal disorders resulting from the presence of altered or abnormal collagen (e.g., Keratoconus). In some embodiments, scaffold formed from the cross-linked extracellular matrix composition can be seeded with cultured corneal epithelial or endothelial cells and can be used in the treatment of corneal dystrophies associated with cornea epithelial layer or endothelial layer with compromised cell regeneration. In some implementations, three scaffolds of cross-linked extracellular matrix composition each seeded with cultured corneal epithelial cells, stromal keratocytes and endothelial cells fused together to construct a cornea-like tissue that can be utilized for the purpose of cornea transplantation.

It is to be understood that, while the examples and figures describe utilizing the extracellular matrix composition and/or gel matrix to stimulate ocular cell growth, the extracellular matrix composition and/or gel matrix can be utilized to stimulate cell regeneration in other tissues as well. One having skill in the art will recognize that the extracellular matrix composition and/or gel matrix can be utilized in the treatment of non-ocular disorders where there is requirement for the presence of an environment rich in healthy extracellular matrix (e.g. ligament repair, treating tissue damage, regenerating burned skin or damaged tissues, treating atrial septal heart defects, etc.).

It is contemplated that the extracellular matrix compositions disclosed herein may also contain one or more conventional antimicrobials (e.g., penicillins, cephalosporins, macrolides, fluoroquinolones, etc.), anti-inflammatories (e.g., corticosteroids), ophthalmic lubricants (e.g. cellulose derivatives); and/or anesthetics (e.g., local anesthetics). The extracellular matrix compositions disclosed may also include one or more pharmaceutically acceptable carriers including, but not necessarily limited to: water, saline, polyethelene glycol, and so forth.

It is further contemplated that, although the examples and figures disclosed herein describe an extracellular matrix composition derived from corneal tissue, the methods and techniques described herein can be utilized with other tissue sources that are rich in extracellular matrix components (e.g., bone tissue, connective tissue, etc.). The tissue source can be selected based on the desired end use of the extracellular matrix composition (e.g., disorder to be treated).

In some embodiments, the seeded extracellular matrix composition and/or seeded gel matrix can be formulated as an injection to be injected at the tissue source where cell regeneration is desired (e.g., the corneal tissue, ligament, burned tissue, etc.). In other embodiments, the extracellular matrix composition and/or gel matrix can be implanted (e.g., as a presolidified matrix seeded with cells into a target tissue) into the desired tissue (e.g., the cornea). In some implementations, the extracellular matrix composition and/or gel matrix can be applied locally with an applicator (e.g., during surgery), or topically.

It is to be understood that embodiments of the present invention described above are intended to be merely exemplary. Those skilled in the art will recognize, or be able to ascertain using no more than routine experimentation, numerous equivalents to the specific procedures described herein. All such equivalents are considered to be within the scope of the present invention and are covered by the following claims.

It is further contemplated that any embodiment or implementation of the disclosure manifested above as a system or method may include at least a portion of any other embodiment or implementation described herein. Those having skill in the art will appreciate that there are various embodiments or implementations by which systems and methods described herein can be implemented, and that the implementation will vary with the context in which an embodiment of the disclosure is deployed.

Furthermore, it is to be understood that although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method of preparing an extracellular matrix composition, comprising:
    extracting one or more corneas from one or more donor sources;

dissolving the one or more corneas in an aqueous solution of inorganic base to form a dissolved cornea solution;

dialyzing the dissolved cornea solution against at least one of a buffer solution or a serum-free medium to remove the inorganic base and adjust the pH of the dissolved cornea to physiological pH;

centrifuging the dissolved cornea solution; and sterilizing the dissolved cornea solution.

2. The method of preparing an extracellular matrix composition of claim 1, wherein the aqueous solution of inorganic base comprises a sodium hydroxide solution.

3. The method of preparing an extracellular matrix composition of claim 1, further comprising seeding the dissolved cornea solution into a pectin-calcium chloride gel to form a gel matrix.

4. The method of preparing an extracellular matrix composition of claim 1, further including seeding the dissolved cornea solution with cultured tissue cells to form a suspension.

5. The method of preparing an extracellular matrix composition of claim 4, wherein the cultured tissue cells comprise at least one of epithelial cells, endothelial cells, or stromal keratocytes.

6. The method of preparing an extracellular matrix composition of claim 1, further comprising cross-linking the dissolved cornea solution to a desired hardness to form a scaffold for sustained regeneration of cells.

7. The method of preparing an extracellular matrix composition of claim 6, further comprising seeding the scaffold with cultured tissue cells.

8. A method of preparing an extracellular matrix scaffold, comprising:

extracting one or more corneas from one or more donor sources;

dissolving the one or more corneas in an aqueous solution of an inorganic base to form a dissolved cornea solution;

dialyzing the dissolved cornea solution against at least one of a buffer solution or a serum-free medium to remove the inorganic base and adjust the pH of the dissolved cornea solution to physiological pH;

centrifuging the dissolved cornea solution;

sterilizing the dissolved cornea solution; and forming a gel matrix from the dissolved cornea solution.

9. The method of preparing an extracellular matrix scaffold of claim 8, wherein dialyzing the dissolved cornea solution against at least one of a buffer solution or a serum-free medium to remove the inorganic base and adjust the pH of the dissolved cornea to physiological pH includes dialyzing the dissolved cornea solution against at least DMEM/F12 medium to remove the inorganic base and adjust the pH of the dissolved cornea to physiological pH.

10. The method of preparing an extracellular matrix scaffold of claim 9, wherein the gel matrix is formed by cross-linking the dissolved cornea solution to a desired hardness.

11. The method of preparing an extracellular matrix scaffold of claim 9, further comprising seeding the scaffold with cultured tissue cells.

12. The method of preparing an extracellular matrix scaffold of claim 11, wherein the cultured tissue cells comprise at least one of epithelial cells, endothelial cells, or stromal cells.

13. The method of preparing an extracellular matrix scaffold of claim 11, wherein the cultured tissue cells comprise cultured corneal cells.

14. The method of preparing an extracellular matrix scaffold of claim 8, wherein sterilizing the dissolved cornea solution comprises exposing the dissolved cornea solution to ultraviolet light.

* * * * *